US010111619B2

(12) United States Patent
Wang (10) Patent No.: US 10,111,619 B2
(45) Date of Patent: Oct. 30, 2018

(54) SMART SPORTS PROTECTIVE APPARATUS INCLUDING USER DATA COLLECTING CIRCUIT

(71) Applicant: Jijun Wang, Beijing (CN)

(72) Inventor: Jijun Wang, Beijing (CN)

( * ) Notice: Subject to any disclaimer, the term of this patent is extended or adjusted under 35 U.S.C. 154(b) by 207 days.

(21) Appl. No.: 15/186,644

(22) Filed: Jun. 20, 2016

(65) Prior Publication Data

US 2017/0007181 A1 Jan. 12, 2017

(30) Foreign Application Priority Data

Jul. 6, 2015 (CN) .......................... 2015 1 0392047

(51) Int. Cl.
*A61B 5/00* (2006.01)
*A63B 71/06* (2006.01)
(Continued)

(52) U.S. Cl.
CPC ............ *A61B 5/6802* (2013.01); *A41D 1/002* (2013.01); *A41D 13/0015* (2013.01);
(Continued)

(58) Field of Classification Search
CPC .. A41D 1/002; A41D 13/0015; A61B 5/0022; A61B 5/02055; A61B 5/021; A61B 5/02416; A61B 5/02438; A61B 5/0402; A61B 5/0488; A61B 5/1112; A61B 5/14551; A61B 5/6802; A61B 5/7271; A61B 5/742; A61B 2560/0214;
(Continued)

(56) References Cited

U.S. PATENT DOCUMENTS

2004/0268286 A1  12/2004  New et al.
2005/0177929 A1* 8/2005  Greenwald ............ A42B 3/046
                                                            2/425
(Continued)

FOREIGN PATENT DOCUMENTS

CN   101890217 A   11/2010
CN   203089109 U    7/2013
(Continued)

OTHER PUBLICATIONS

European Search Report dated Dec. 2, 2016, by the European Patent Office.
(Continued)

*Primary Examiner* — Michael Carey
(74) *Attorney, Agent, or Firm* — Dilworth & Barrese, LLP.; Michael J. Musella, Esq.

(57) ABSTRACT

According to some embodiments of this disclosure, a smart sports protective apparatus comprises: a base body device for covering at least a part of a user's body to relieve an impact of an external force to at least the part of the user's body when the user is playing sports; a circuit device for collecting user data, including the user's biological data, motion status data, and body gesture data, from the user in real time when the user is playing sports, at least a part of the circuit device being arranged inside the base body device; and a power supply device for supplying an electric power to the circuit device, the power supply device being arranged inside the base body device.

15 Claims, 6 Drawing Sheets

(51) Int. Cl.
| | |
|---|---|
| *A63B 71/12* | (2006.01) |
| *A63B 24/00* | (2006.01) |
| *A41D 1/00* | (2018.01) |
| *A41D 13/00* | (2006.01) |
| *A61B 5/0205* | (2006.01) |
| *A61B 5/0402* | (2006.01) |
| *A61B 5/0488* | (2006.01) |
| *A61B 5/11* | (2006.01) |
| *A61B 5/1455* | (2006.01) |
| *A63B 71/10* | (2006.01) |
| *A61B 5/021* | (2006.01) |
| *A61B 5/024* | (2006.01) |

(52) U.S. Cl.
CPC ........ *A61B 5/0022* (2013.01); *A61B 5/02055* (2013.01); *A61B 5/0402* (2013.01); *A61B 5/0488* (2013.01); *A61B 5/1112* (2013.01); *A61B 5/14551* (2013.01); *A61B 5/7271* (2013.01); *A61B 5/742* (2013.01); *A63B 24/0062* (2013.01); *A63B 71/06* (2013.01); *A63B 71/10* (2013.01); *A63B 71/1225* (2013.01); *A61B 5/021* (2013.01); *A61B 5/02416* (2013.01); *A61B 5/02438* (2013.01); *A61B 2560/0214* (2013.01); *A61B 2560/0242* (2013.01); *A61B 2562/0219* (2013.01); *A61B 2562/0223* (2013.01); *A63B 2071/125* (2013.01); *A63B 2071/1266* (2013.01); *A63B 2220/12* (2013.01); *A63B 2220/13* (2013.01); *A63B 2220/44* (2013.01); *A63B 2220/56* (2013.01); *A63B 2220/73* (2013.01); *A63B 2220/836* (2013.01); *A63B 2225/50* (2013.01); *A63B 2230/04* (2013.01); *A63B 2230/06* (2013.01); *A63B 2230/207* (2013.01); *A63B 2230/30* (2013.01); *A63B 2230/50* (2013.01)

(58) Field of Classification Search
CPC .... A61B 2560/0242; A61B 2562/0219; A61B 2562/0223; A63B 24/0062; A63B 71/06; A63B 71/10; A63B 71/1225; A63B 2071/125; A63B 2071/1266; A63B 2220/12; A63B 2220/13; A63B 2220/44; A63B 2220/56; A63B 2220/73; A63B 2220/836; A63B 2225/50; A63B 2230/04; A63B 2230/06; A63B 2230/207; A63B 2230/30; A63B 2230/50
USPC .................................................. 600/300, 301
See application file for complete search history.

(56) References Cited

U.S. PATENT DOCUMENTS

| | | | |
|---|---|---|---|
| 2009/0030289 A1* | 1/2009 | Katayama | A61B 5/0008 600/301 |
| 2013/0130843 A1* | 5/2013 | Burroughs | A63B 71/0686 473/415 |
| 2013/0166049 A1 | 6/2013 | Werner et al. | |
| 2013/0274587 A1* | 10/2013 | Coza | A61B 5/6804 600/409 |
| 2015/0094551 A1 | 4/2015 | Frix et al. | |
| 2015/0366504 A1* | 12/2015 | Connor | A61B 5/6804 600/301 |
| 2016/0206242 A1* | 7/2016 | Esposito | A61B 5/1038 |

FOREIGN PATENT DOCUMENTS

| | | |
|---|---|---|
| CN | 204189197 U | 3/2015 |
| CN | 104706359 A | 6/2015 |
| CN | 205019686 U | 2/2016 |
| EP | 2654030 A1 | 10/2013 |
| JP | 2004048361 A | 2/2004 |
| JP | 2008173462 A | 7/2008 |
| JP | 2013521086 A | 6/2013 |
| JP | 2013135849 A | 7/2013 |
| JP | 2014500740 A | 1/2014 |
| JP | 2014140400 A | 8/2014 |
| JP | 2014166589 A | 9/2014 |
| KR | 20100032273 A | 3/2010 |
| KR | 101140544 B1 | 5/2012 |
| WO | 2007033194 A2 | 3/2007 |
| WO | 2012061438 A2 | 5/2012 |
| WO | 2012092524 A3 | 7/2012 |
| WO | 2014190013 A1 | 11/2014 |
| WO | 2015021393 A1 | 2/2015 |
| WO | 2015054312 A1 | 4/2015 |

OTHER PUBLICATIONS

EP Communication: the Communication issued by EPO for the European patent application (No. 16174771.2) dated Nov. 27, 2017.
JP Decision of Refusal; the Decision of Refusal issued by JPO for the Japanese counterpart (Application No. 2016-121275) dated Jan. 30, 2018.
KR Notice of Final Rejection: the Notice of Final Rejection issued by KIPO for the Korean counterpart application (Application No. 10-2016-0083600) dated Dec. 26, 2017.
Chinese Office Action dated May 19, 2017.
Japanese Search Report dated Apr. 14, 2011.
Notice of Preliminary Rejection issued by the Korean International Patent Office dated Jun. 21, 2017.
Notice of Reason for Rejection issued by the Japanese Patent Office dated May 24, 2017.
Chinese Office Action dated Nov. 1, 2016, by the Chinese Patent Office.

\* cited by examiner

SMART SPORTS PROTECTIVE APPARATUS INCLUDING USER DATA COLLECTING CIRCUIT

CROSS REFERENCE

The present application claims the benefit of, and priority to, Chinese Patent Application No. 201510392047.1, entitled "SMART SPORTS PROTECTIVE APPARATUS", filed on Jul. 6, 2015, the disclosure of which is incorporated herein in its entirety by reference.

TECHNICAL FIELD

This disclosure relates to the field of wearable devices, and more particularly, to a smart sports protective apparatus.

BACKGROUND

A conventional sports protective apparatus is an appliance commonly used in sports games and training to disperse and buffer pressure and impulse force applied to an athlete so as to protect the athlete from physical injuries. However, it has no further functions and cannot meet requirements of modern sports. For example, in modern sports, it is expected to detect the athlete's relevant data during the games and training so as to provide a scientific reference for the athlete's training and evaluation.

For this reason, the athlete usually needs to wear a general-purpose smart wearable device (for example, a conventional smart hand ring) in addition to the protective apparatus, and use the device to monitor real-time data related to the athlete's exercising, sleeping, diet, or the like in his/her everyday life, so as to guide his/her training by using such data.

However, the general-purpose smart wearable device has poor accuracy in data measurement, and sensors and techniques adopted therein are usually relatively unitary, so that requirements of professional training and evaluation cannot be met. For example, at present, the general-purpose smart wearable device usually adopts an acceleration sensor to calculate the athlete's displacement and velocity, which will cause a relatively large measurement error and thus make it impossible to help the athlete improve his/her skill level accurately.

SUMMARY

In order to solve the above-described technical problems, according to one aspect of this disclosure, there provides a smart sports protective apparatus, comprising: a base body device for covering at least a part of a user's body to relieve an impact of an external force to at least the part of the user's body when the user is playing sports; a circuit device for collecting user data, including the user's biological data, motion status data, and body gesture data, from the user in real time when the user is playing sports, at least a part of the circuit device being arranged inside the base body device; and a power supply device for supplying an electric power to the circuit device, the power supply device being arranged inside the base body device.

In one embodiment of this disclosure, the smart sports protective apparatus is a smart leg guard, in which the base body device covers at least a part of the user's shank to relieve the impact of the external force to the user's shank when the user is playing sports, so as to prevent the user's shank from being injured.

In one embodiment of this disclosure, the smart sports protective apparatus is a smart wrist guard, a smart knee guard, or a smart headband, in which the base body device covers at least a part of the user' wrist, knee, or head, to relieve the impact of the external force to the user's wrist, knee, or head when the user is playing sports, so as to prevent the user's wrist, knee, or head from being injured.

In one embodiment of this disclosure, the circuit device comprises: a data collecting unit for collecting the user data, and the data collecting unit including a biosensing module for collecting the user's biological data, a gesture sensing module for collecting the user's body gesture data, and a motion sensing module for collecting the user's motion status data; and a first processing unit for controlling the collecting operations of the data collecting unit.

In one embodiment of this disclosure, at least a part of the biosensing module is arranged on an inner surface of the base body device contacting with the user's body, and the biosensing module comprises at least one of a heart rate sensor for detecting data of a real-time heart rate of the user, an electrocardio sensor for detecting data of a real-time electrocardio of the user, a pulse sensor for detecting data of a real-time pulse of the user, a blood oxygen sensor for detecting data of a real-time blood oxygen of the user, a body temperature sensor for detecting data of a real-time body temperature of the user, a myoeletricity sensor for detecting data of a real-time myoeletricity of the user, and a blood pressure sensor for detecting data of a real-time blood pressure of the user.

In one embodiment of this disclosure, at least one of the heart rate sensor, the electrocardio sensor, the pulse sensor, and the blood oxygen sensor comprises an optical transceiver which, when the base body device covers at least the part of the user's body, emits and receives light in a closed space formed by the base body device and at least the part of the user's body without being influenced by external light.

In one embodiment of this disclosure, the myoeletricity sensor comprises two electrodes provided at the same height and at two outermost edges of the inner surface respectively.

In one embodiment of this disclosure, the gesture sensing module is provided between an inner surface of the base body device contacting with the user's body and an outer surface of the base body device not contacting with the user's body, and the gesture sensing module comprises at least one of a gyroscope sensor for detecting data of a real-time inclination and rotation angle of the user, an acceleration sensor for detecting data of a real-time acceleration of the user, a geomagnetic field sensor for detecting data of a real-time orientation or direction of the user, and an air pressure sensor for detecting data of a real-time altitude and air pressure of the user.

In one embodiment of this disclosure, at least a part of the motion sensing module is provided between an inner surface of the base body device contacting with the user's body and an outer surface of the base body device not contacting with the user's body, and the motion sensing module comprises a satellite signal receiver for receiving satellite signals from a plurality of satellite signal transmitters, so as to determine data of a real-time position of the user according to signal parameters of the satellite signals respectively received from the plurality of satellite signal transmitters and known data of positions of the plurality of satellite signal transmitters.

In one embodiment of this disclosure, the satellite signal receiver and the plurality of satellite signal transmitters comply with a global positioning system (GPS) standard.

In one embodiment of this disclosure, the circuit device further comprises a storing unit for storing the user data.

In one embodiment of this disclosure, the circuit device further comprises a first wireless communication unit for transmitting the user data to a mobile terminal wirelessly.

In one embodiment of this disclosure, the first wireless communication unit complies with at least one of communication standards including Bluetooth® and wireless Fidelity (Wi-Fi). In one embodiment of this disclosure, the first wireless communication unit complies with at least one of communication standards including Bluetooth® and wireless Fidelity (Wi-Fi).

In one embodiment of this disclosure, the circuit device further comprises: a second wireless communication unit for transmitting the user data to a server wirelessly via a base station apparatus, so that based on the user data, the server performs at least one of displaying the user data at a specific time, calculating the user's displacement during a specific time period, calculating the user's velocity at a specific time, calculating the user's average velocity during a specific time period, calculating the user's maximum velocity and minimum velocity during a specific time period, calculating the user's acceleration at a specific time, drawing the user's moving track during a specific time period, analyzing the user's physiological status at a specific time, presenting the user's body gesture at a specific time, analyzing a performance quality and a timeliness of the user's specific skilled action, and evaluating the user's athletic ability, skill level, and/or training result; and a second processing unit for controlling the wireless transmission operation of the second wireless communication unit.

In one embodiment of this disclosure, the second wireless communication unit further transmits beacon data to a plurality of base station apparatus, so as to determine data of a real-time position of the user according to signal parameters of the beacon data respectively received by the plurality of base station apparatus and known data of positions of the plurality of base station apparatus.

In one embodiment of this disclosure, the second wireless communication unit and the base station apparatus comply with at least one of communication standards including ultra wide band (UWB), chirp spread spectrum (CSS), mobile communication.

In one embodiment of this disclosure, the second wireless communication unit comprises: a radio frequency module for converting data to be transmitted into a radio-frequency signal in real time, the data to be transmitted including the user data or the beacon data; and an antenna module for radiating the radio-frequency signal outwards, the antenna module being provided on an outer surface of the base body device not contacting with the user's body.

In one embodiment of this disclosure, the antenna module is printed or embedded on the outer surface directly in a form of a flexible circuit.

In one embodiment of this disclosure, the circuit device further comprises a power managing unit for selectively supplying the electric power from the power supply device to the first processing unit and/or the second processing unit according to the user's usage requirement.

In one embodiment of this disclosure, the circuit device and the power supply device are formed integrally, and are tiled in the same direction in the base body device.

In one embodiment of this disclosure, the circuit device and the power supply device are provided in the base body device in a detachable manner.

Adopting the smart sports protective apparatus according to the embodiments of this disclosure can conveniently collect the user's related real-time data for later analysis while protecting the user's body from injuries without adding additional equipment, so as to provide a scientific reference for the user's training and evaluation.

Other characteristics and advantages of this disclosure are explained in the subsequent specification, are obvious partly from the specification, and can be understood by implementing this disclosure. Objects and other advantages of the present disclosure can be implemented and obtained by structures specified particularly in the specification, the claims, and the accompanying drawings.

DETAILED DESCRIPTION OF THE PREFERRED EMBODIMENT

Various embodiments according to this disclosure will be described in detail with reference to the accompanying drawings. Here, it is noted that the same reference number are given to constituent parts having substantially the same or similar structures and functions, and repetitive descriptions thereof are omitted.

With respect to the existing technical problems in which, on one hand, a conventional sports protective apparatus has no functions other than reducing sports injuries to an athlete's body; and on the other hand, a general-purpose smart wearable device has poor accuracy in data measurement and thus cannot be applied in a professional sports training and evaluation, the inventor realizes that an intelligentized reconstruction can be performed on the conventional sports protective apparatus, so that in addition to injury prevention, the apparatus can monitor the athlete's sports activities accurately, so as to help the athlete carry out a scientific training and evaluation with informationized, visualized and digitized monitoring.

Hereinafter, a schematic diagram of a structure of a smart sports protective apparatus according to embodiments of this disclosure will be described with reference to FIG. 1.

Figure 1:
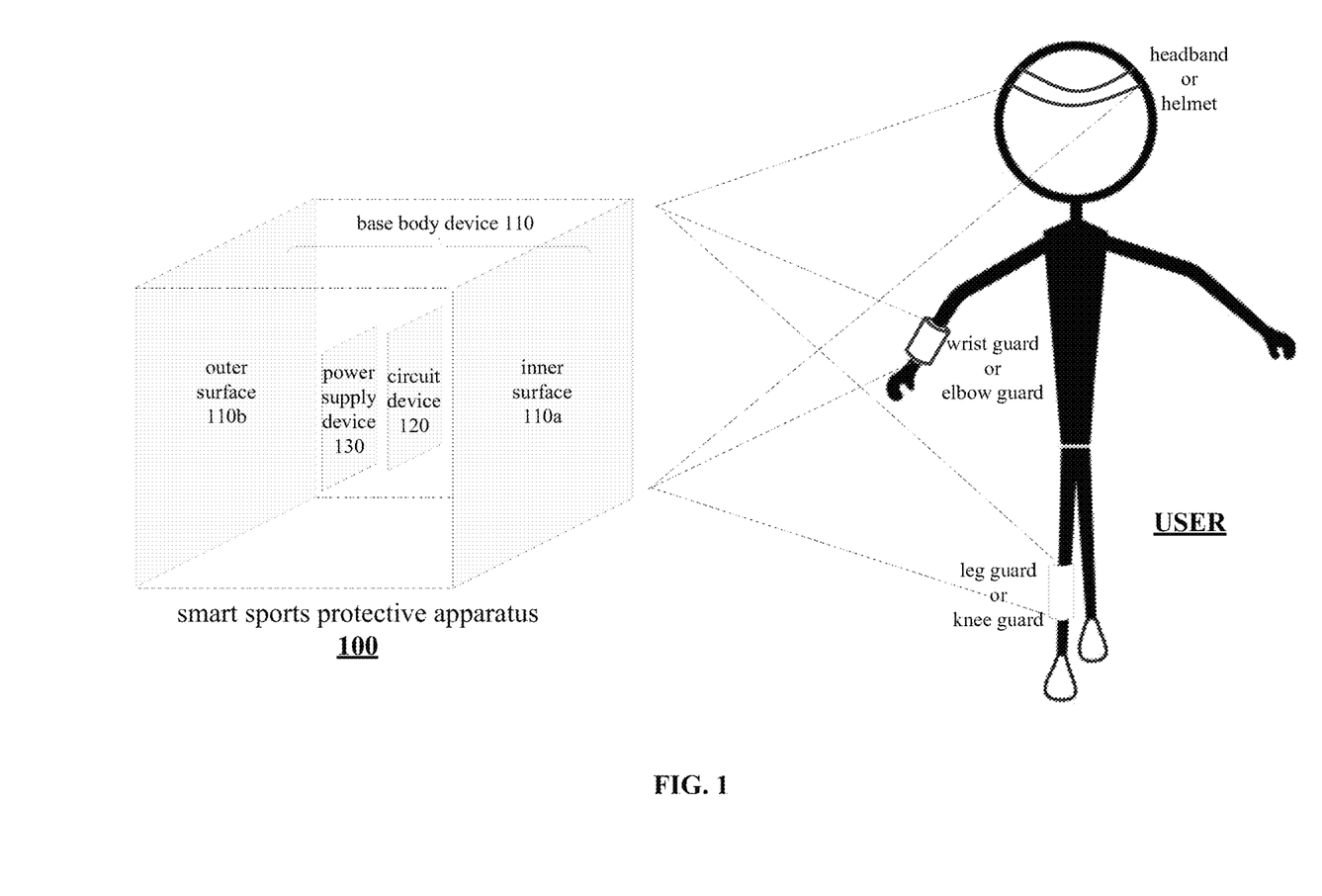
FIG. 1 illustrates a schematic diagram of a smart sports protective apparatus according to embodiments of this disclosure.

FIG. 1 illustrates a schematic diagram of a smart sports protective apparatus according to embodiments of this disclosure.

As shown in FIG. 1, a smart sports protective apparatus 100 includes a base body device 110, a circuit device 120 and a power supply device 130.

The base body device 110 can cover at least a part of a user's body (e.g., the user may be an athlete, a ballplayer, a trainee, or anyone else) to relieve an impact of an external force to at least the part of the user's body when the user is playing sports. Obviously, this can protect and prevent the user's body from injuries such as a bone fracture. For example, the user's body may be the user's head and neck, trunk (for example, breast, stomach, back, crotch, or the like), limbs (hand, wrist, arm, shoulder, leg, ankle, foot, or the like), and so on.

At least a part of the circuit device 120 can be arranged inside the base body device 110, and the circuit device 120 can collect user data, including the user's biological data, motion status data, and body gesture data, from the user in real time when the user is playing sports.

The power supply device 130 can be arranged inside the base body device 110, and supply an electric power to the circuit device 120. In one example, the power supply device 130 is a power supply and managing device for supplying the electric power to the circuit device 120 and managing distribution of the electric power among respective system components.

As shown in FIG. 1, the apparatus 100 can be various kinds of sports protective apparatus for protecting respective parts of the user's body from sports injuries. For example, it includes, but is not limited to: a head guard, a shoulder protector, a hand protector, an elbow guard, a wrist guard, a waist protector, a leg guard, a knee guard, an ankle guard, a combined sports protector, or other sports protective apparatus.

In one embodiment, the apparatus 100 can be a smart leg guard for protecting a user's shank. In this case, the base body device 110 can cover at least a part of the user's shank to relieve the impact of the external force to at least the part of the user's shank when the user is playing sports, so as to prevent the user's shank from injuries such as a bone fracture. Obviously, this disclosure is not limited to this. As explained above, the apparatus 100 can also be other sports protective apparatus such as a smart wrist guard, a smart knee guard, or a smart headband for protecting the user's wrist, knee, or head, respectively.

In the embodiments of this disclosure, in order to achieve a better protecting effect, in the apparatus 100, a shape of the base body device 110 can be designed to be suitable for covering the user's body.

For example, in the case that the apparatus 100 is a leg guard, the base body device 110 has a shape matched with an arc-shaped surface of the user's shank. That is, the base body device 110 has a curved transversal section and a longitudinal section of a certain length, so as to shield most or all areas of the user's shinbone.

Next, as shown in FIG. 1, the apparatus 100 includes at least two surfaces of an inner surface 110a and an outer surface 110b.

The inner surface 110a is a surface contacting with the user's body. Preferably, in order to achieve a better user protection, the apparatus 100 can be fixed onto the user's body with a relatively strong force so as to avoid falling-off. Such force makes the inner surface 110a attached onto the user's body tightly, so that a relative closed environmental space is formed between the inner surface 110a and the skin on the user's body.

For this reason, the apparatus 100 can also include a fixing device (not shown) for fixing the base body device 110 onto at least the part of the user's body. For example, the fixing device can be a binding band, a Velcro® strap, or the like.

The outer surface 110b is a surface not contacting with the user's body. That is, the outer surface 110b and the inner surface 110a are two opposite surfaces of the smart sports protective apparatus 100. Preferably, the outer surface 110b can be made of wear-resistant material.

In the embodiments of this disclosure, in order to enable the sports protective apparatus 100 to intelligently monitor the user's conditions when the user is playing sports, so as to help the user carry out a scientific training and evaluation with informationized, visualized and digitized monitoring, the apparatus 100 is equipped with the circuit device 120 which can collect the user's biological data, motion status data, and body gesture data at the time of playing sports (for example, when the user is playing games, taking training, or even resting).

Figure 2:
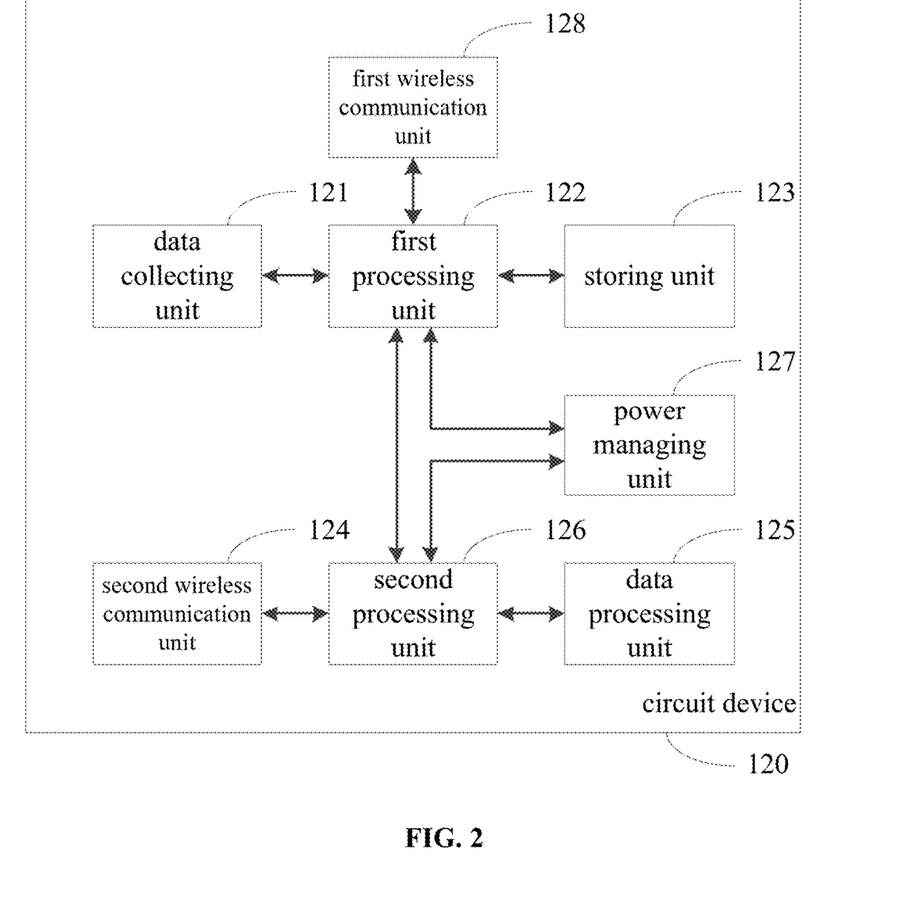
FIG. 2 illustrates a schematic diagram of a circuit device according to the embodiments of this disclosure.

FIG. 2 illustrates a schematic diagram of a circuit device 120 according to the embodiments of this disclosure.

As shown in FIG. 2, the circuit device 120 includes a data collecting unit 121 and a first processing unit 122.

The data collecting unit 121 can collect user data including the user's biological data, motion status data, and body gesture data.

The first processing unit 122 can control the collecting operation of the data collecting unit 121. Further, the first processing unit 122 can also control a pre-processing operation related to the data collected by the data collecting unit 121. For example, the pre-processing operation may be operations of amplifying, filtering, denoising and digital-analog conversion of the collected data.

In one embodiment, the data collecting unit 121 includes a plurality of independent sensing modules. However, the present disclosure is not limited to this. Obviously, the data collecting unit 121 can also be constituted by a single sensing module having various kinds of data collecting functions.

Figure 3:
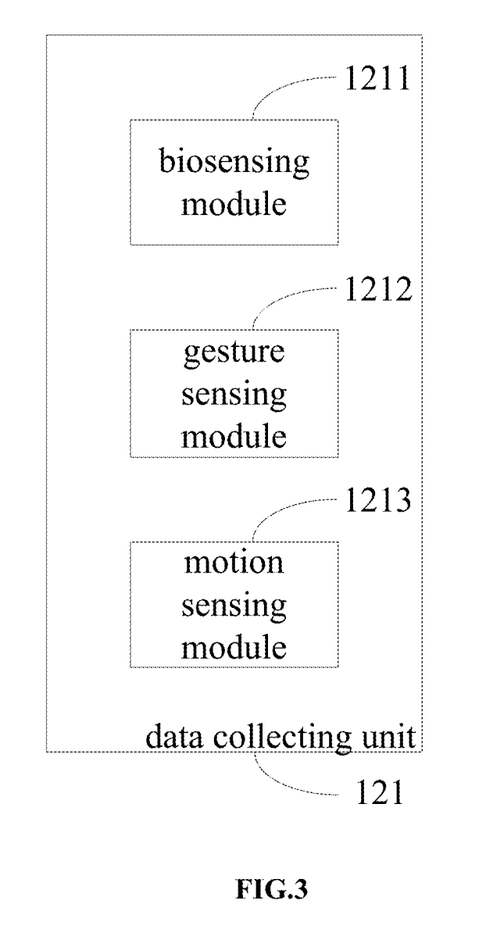
FIG. 3 illustrates a schematic diagram of a data collecting unit according to the embodiments of this disclosure.

FIG. 3 illustrates a schematic diagram of a data collecting unit 121 according to the embodiments of this disclosure.

As shown in FIG. 3, the data collecting unit 121 includes a biosensing module 1211 for collecting the user's biological data, a gesture sensing module 1212 for collecting the user's body gesture data, and a motion sensing module 1213 for collecting the user's motion status data.

Depending on respective functions of each sensing module, the biosensing module 1211, the gesture sensing module 1212, and the motion sensing module 1213 can be located in different positions of the base body device 110.

In order to collect the user's biological data, at least a part of the biosensing module 1211 can be in contact with the user's body to implement functions of collecting biological signals (physiological signals, vital sign signals) and converting the same into electrical signals.

For example, in one embodiment, at least a part of the biosensing module 1211 is arranged on the inner surface 110a of the base body device 110, and the biosensing module 1211 can includes at least one of a heart rate sensor for detecting data of a real-time heart rate of the user, an electrocardio sensor for detecting data of a real-time electrocardio of the user, a pulse sensor for detecting data of a real-time pulse of the user, a blood oxygen sensor for detecting data of a real-time blood oxygen of the user, a body temperature sensor for detecting data of a real-time body temperature of the user, a myoeletricity sensor for detecting data of a real-time myoeletricity of the user, a blood pressure sensor for detecting data of a real-time blood pressure of the user, and the like.

In one embodiment, the biosensing module 1211 can be a sensor adopting a photo-electric transmission measuring method, which measures the biological data by using changes in absorbance of blood hemoglobin in a blood vessel, for example, uses a beam emission circuit and a reflection reception circuit of green light and infrared light to measure the user's heart rate, electrocardio, pulse, blood oxygen content, or the like.

That is, at least one of the heart rate sensor, the electrocardio sensor, the pulse sensor, and the blood oxygen sensor includes an optical transceiver, which emits and receives light in a closed space formed by the base body device and at least the part of the user's body without being influenced by external light when the base body device covers at least the part of the user's body. In this case, the optical transceiver can be provided on the inner surface 110a so as to detect the biological data in an optical manner.

In another embodiment, the biosensing module 1211 can also be a sensor adopting a electrocardio measuring method, which senses changes in cardioelectricity generated every time a human's heart beats to measure the biological data, for example uses pole pieces of the sensor to collect a fluctuation magnitude of the cardioelectricity of the user, and then transmits it to a processing chip using wired or wireless transmission techniques, so as to convert it into a numerical value of beats per minute (BPM), which is easy to be observed.

That is, at least one of the heart rate sensor, the electrocardio sensor, the pulse sensor, and the myoelectricity sensor includes two electrodes contacting with the skin on the user's body without being influenced by external interference when the base body device covers at least the part of the user's body. In this case, the two electrodes can be provided on the inner surface 110a. Preferably, they are provided at the same height and at two outermost edges of the inner surface 110a respectively, so that a distance between them is largest so as to increase the accuracy of the detection.

In another embodiment, the biosensing module 1211 can also be a blood pressure sensor adopting an oscillometry method. The blood pressure sensor includes an air charging and discharging component and a wave detecting component for acquiring oscillatory waves generated during air discharging and converting the same into values of the blood pressure by using a certain algorithm.

Alternatively, the biosensing module 1211 can also be a body temperature sensor for measuring the user's body temperature based on a principle that solid, liquid or gas has thermal expansion and contraction influenced by temperature, a principle that a pressure of gas (or vapor) changes with temperature in a condition of constant volume, a principle that a resistance changes with temperature, or the like.

Although the biosensing, module 1211 has been explained by some examples above, this disclosure is not limited thereto. Obviously, the biosensing module 1211 can also be other bio-sensors.

Thus, by using various kinds of physiological information sensor built in the system, the athlete's real-time physiological information, including but not limited to the heart rate, the pulse, the blood oxygen, the blood pressure, the electrocardio, the body temperature, condition of muscle, or the like, can be collected.

Hereinafter, for clarity, a detail configuration of the biosensing module 1211 will be described in detail in one specific example with reference to FIG. 4. In the specific example, it assumes that the smart sports protective apparatus is a leg guard. It is obvious that, without redundant description, the configuration of the biosensing module 1211 can also be applied in other sports protective apparatus such as a wrist guard, a knee guard, or the like.

Figure 4:
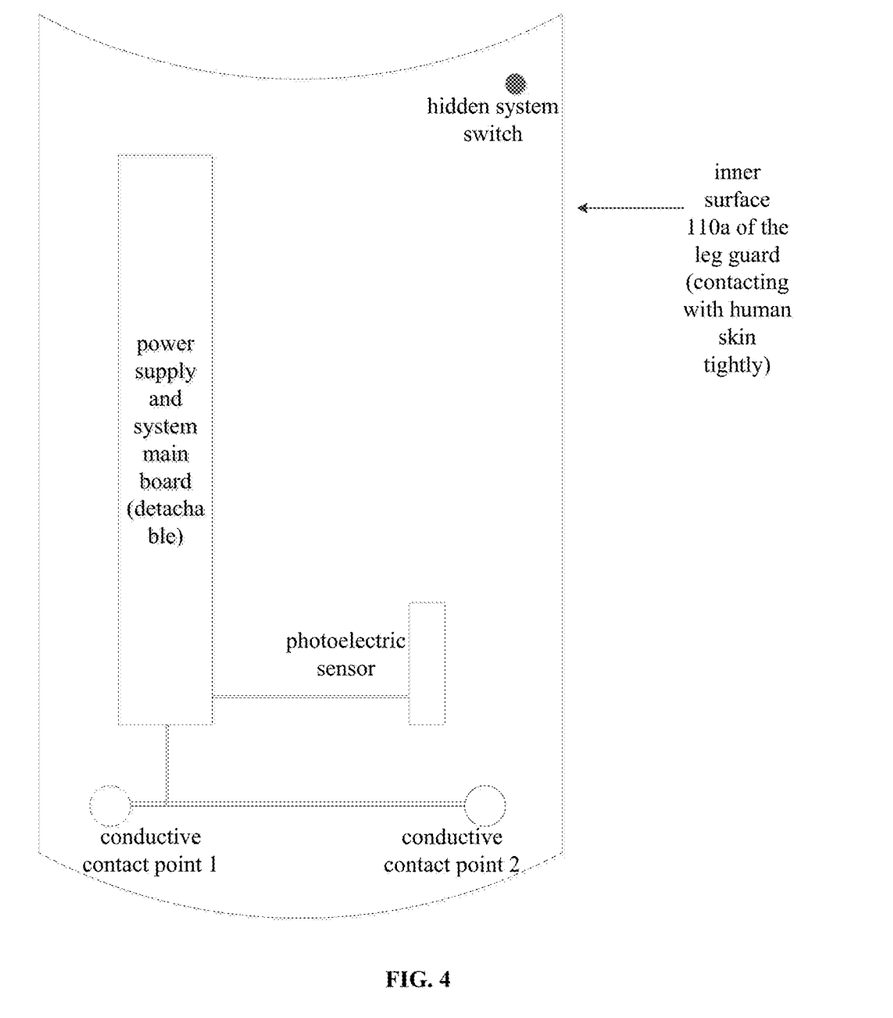
FIG. 4 illustrates a schematic diagram of a biosensing module according to a specific example of the embodiments of this disclosure.

FIG. 4 illustrates a schematic diagram of a biosensing module according to a specific example of the embodiments of this disclosure.

With reference to FIG. 4, a photoelectric sensor is provided in the middle area of the inner surface 110a of the smart leg guard. By positioning a photoelectric sensor for collecting physiological signals on the inner surface of the leg guard, related physiological information can be measured accurately based on the principle that blood vessels have different reflectance to light of different wave bands. And, a tight fit formed between the leg guard and the user's leg after the leg guard is worn can make the sensor be in a relative closed environment in which reflective interference of other light-sources does not exist, so that the sensor can operate in an ideal environment. Thus, the measurement procedure is reliable and thus the collected physiological data is accurate.

Further, as shown in FIG. 4, two conductive contact points (electrodes or pole pieces) are respectively arranged at left and right edges and at the same height in a lower area of the inner surface 110a of the smart leg guard. For example, these two conductive contact points can collect bio-electricity signals to perform myoelectricity analysis so as to obtain the condition of muscle. Since the distance between the two conductive contact points is the largest, sensitivity for sensing the bio-electric current is maximized, so that the accuracy of the detection is maximized.

Further, with reference to FIG. 4, in order to turn on/off the leg guard easily, a system switch can be arranged on the inner surface 110a of the leg guard (for example, at the upper right corner of the leg guard, as shown in FIG. 4). However, if the system switch protrudes from the inner surface 110a, the user wearing the leg guard may have an uncomfortable feeling at the corresponding position of his/her leg, the user's skin may be chafed, and the system switch may be easily operated by accident. For this reason, the system switch can be provided as a hidden system switch (i.e., not protruding from the inner surface), so that the inner surface of the leg guard is still a smooth curved surface without any protruding structure.

In the embodiments of this disclosure, since the gesture sensing module 1212 does not need to contact with the user's body directly, it can be arranged in the interior of the base body device 110, so as to utilize the mechanical strength of the sports protective apparatus as much as possible to ensure that it is not damaged due to the external force.

In one embodiment, the gesture sensing module 122 can be provided between the inner surface 110a and the outer surface 110b, and include at least one of a gyroscope sensor for detecting data of a real-time inclination and rotation angle of the user, an acceleration sensor for detecting data of a real-time acceleration of the user, a geomagnetic field sensor for detecting data of a real-time orientation or direction of the user, an air pressure sensor for detecting data of a real-time altitude and air pressure of the user, and the like. Obviously, this disclosure is not limited to this. The gesture sensing module 1212 can be other known gesture sensors.

Thus, by using the related gesture sensor built in the system, the athlete's body gesture data can be collected in real time, and the athlete's body gesture can be presented in real time in combination with gesture presenting algorithms and data models.

In the embodiments of this disclosure, at least a part of the motion sensing module 1213 can be provided between the inner surface 110a and the outer surface 110b. Preferably, when the motion sensing module 1213 needs to receive wireless signals from outside or transmit wireless signals outwards, at least a part of the motion sensing module 1213 is arranged not to be blocked by insulators in the apparatus 100 as much as possible, so as to increase intensity of transmission and reception of the wireless signals. In contrary, when the motion sensing module 1213 does not need to transmit or receive wireless signals, it can be completely positioned inside the base body device 110 to prevent damage.

In one embodiment, the motion sensing module 1213 includes a satellite signal receiver for receiving, from a plurality of satellite signal transmitters, satellite signals for a real-time positioning operation of the user. The real-time positioning operation can determine data of a real-time position of the user according to signal parameters of the satellite signals respectively received from the plurality of satellite signal transmitters and data of positions of the plurality of satellite signal transmitters. For example, the satellite signal receiver and the satellite signal transmitters can comply with a global positioning system (GPS) standard.

Structurally, for example, the satellite signal receiver can include an antenna module and a calculating module. At this time, at least the antenna module of the satellite signal receiver is provided on the outer surface 110b, to prevent components in the base body device 110 from blocking the antenna module so as to cause attenuation of the wireless signal. Of course, in order to prevent the antenna module from being damaged, it can also be arranged inside the smart sports protective apparatus as long as the reception intensity of the satellite signal is acceptable.

In particular, the satellite signals transmitted by the plurality of satellite signal transmitters (for example, geosynchronous orbit satellites, geo stationary orbit satellites) are received by the satellite signal receiver (e.g., the GPS receiver) of the smart sports protective apparatus, and adopting a spatial distance resection method, the calculating module determines a position of a point to be measured by using instant positions of the satellites moving in a high speed as known initial data for calculation.

Although the motion sensing module 1213 is described using the GPS positioning principle, obviously this disclosure is not limited thereto. For example, the motion sensing module 1213 can also be other motion sensors based on wireless signal transmission, or even motion sensors not based on the wireless signal transmission, such as a motion sensor based on an accelerometer or the like.

Next, with reference back to FIG. 2, the circuit device 120 can further include one of more of a storing unit 123, a first wireless communication unit 128, a second wireless communication unit 124, a data processing unit 125, a second processing unit 126, and a power managing unit 127.

In one embodiment, after the data collecting unit 121 collects the user data including the user's biological data, motion status data, and body gesture data under the control of the first processing unit 122, the user data can be stored in the storing unit 123 located locally in the smart sports protective apparatus 100 to prevent the data from being lost. That is, the storing unit 123 can store the user data collected by the data collecting unit 121. Further, the storing unit 123 can also store operation data of the entire system of the smart sports protective apparatus.

For example, the storing unit 123 can includes an electrical connection having one or more conducting wires, a portable disk, a hard disk, a random access memory (RAM), an erasable programmable read only memory (EPROM or a flash memory), an optical fiber, a compact disc read-only memory (CD-ROM), a light storage device, a magnetic storage device, or any suitable combination thereof.

In one embodiment, in order to view the user data collected in real time, the user data can be uploaded to a mobile terminal such as a mobile telephone, a personal digital assistant (PDA), a tablet computer (PAD), a portable computer or the like in a wired and/or wireless manner (preferably, wirelessly). For this reason, the first wireless communication unit 128 can transmit the user data to the mobile terminal wirelessly.

The smart sports protective apparatus can adopt various kinds of communication protocols to communicate with the mobile terminal. For example, the first wireless communication unit can comply with at least one of communication standards including Bluetooth® and wireless Fidelity (Wi-Fi). That is, the first wireless communication unit 128 can include communication modules such as a Bluetooth® module, a Wi-Fi® module, or the like.

Structurally, for example, the first wireless communication unit 128 can include a radio frequency unit and an antenna module. At this time, at least the antenna module is provided on the outer surface 110b, to prevent possible attenuation of the wireless signals caused by components in the base body device 110.

Further, in one embodiment, the mobile terminal can upload the user data to a server in a wired and/or wireless manner (preferably, wirelessly), to perform analysis, organization, simulation, or the like on the user data in the server. For this reason, the second wireless communication unit 124 can transmit the user data to the server wirelessly via a base station apparatus, so that based on the user data, the server can perform at least one of displaying the user data at a specific time, calculating the user's displacement during a specific time period, calculating the user's velocity at a specific time, calculating the user's average velocity during a specific time period, calculating the user's maximum velocity and minimum velocity during a specific time period, calculating the user's acceleration at a specific time, drawing the user's moving track during a specific time period, analyzing the user's physiological status at a specific time, presenting the user's body gesture at a specific time, analyzing a performance quality and a timeliness of the user's specific skilled action, evaluating the user's athletic ability, skill level, and/or training result, and the like.

The apparatus 100 can adopt various kinds of communication protocols to communicate with the server. For example, the second wireless communication unit 124 can comply with at least one of communication standards such as ultra wide band (UWB), chirp spread spectrum (CSS), mobile communication (2G/3G/4G/5G), or the like. Additionally, the server can be a standalone centralized server for implementing collection and analysis of various types of data. Alternatively, such server can also include: clusters of distributed servers for implementing the data collection and analysis respectively, and one or more centralized server for aggregating all relevant data and evaluating the athlete's various parameters based on such data comprehensively.

Thus, the smart sports protective apparatus 100 according to the embodiments of this disclosure can not only collect the athlete's biological data, motion status data, and body gesture data in real time by various kinds of related sensors built in the system, but also transmit the related data collected as required in real time or non-real time to an analyzing server (e.g., at cloud end) through a series of hardware apparatus, algorithms, and software platforms, so that the analyzing server can further analyze the performance quality and the timeliness of the athlete's certain skilled action in real time in combination with sports evaluating algorithm, so as to achieve a comprehensive analysis. In particular, the analyzing server can analyze all data in the entire procedure of the games and training comprehensively to evaluate the athlete's skill level and training result precisely, so as to help the athlete improve his/her sports performance fast.

For example, according to data collected by the apparatus 100 in the games or the training, the analyzing server can detect a running distance, a running velocity, a running velocity at a moment of passing the ball, times of running, a velocity of swinging the leg to kick the ball, a strength of muscle, times of falling to ground, a velocity of turning-around, or the like of the athlete in real time, and can detect physical indices of the athlete's blood oxygen, blood pressure, and heart rate during each period of time, so as to provide training or evaluation data to the athlete's coach, trainer, parents, or the like, to help them analyze the athlete's history data, so as to help the athlete make progress, identify enhancement of the athlete's performance, find a talent with high potential, and so on.

Preferably, in one embodiment, in addition to transmitting the collected user data and/or other data related to the apparatus 100 to the server, the second wireless communication unit 124 can also interact with the base station apparatus to implement a positioning operation of the user in playing sports with high precision. For this reason, the second wireless communication unit 124 can transmit beacon data for real-time positioning operation of the user to a plurality of base station apparatus, and the real-time positioning operation can determine data of the user's real-time position at the time of playing sports according to signal parameters of the beacon data received respectively by the plurality of base station apparatus and data of the positions of the plurality of base station apparatus.

Preferably, for example, at the time of the high-accuracy positioning, the second wireless communication unit 124 can comply with the communication standard of ultra wide band (UWB). In particular, a UWB impulse signal transmitted by the second wireless communication unit 124 (also referred as an electronic tag) is received by a plurality of positioning base stations (also referred as anchor points), then each of the plurality of positioning base stations can transmit characteristics (for example, an intensity, an arrival time, an angle of arrival, or the like) of the received impulse signal to a positioning server, and the positioning server can determine coordinates of the athlete's real-time position in the sports field to position the athlete by using known coordinates of the positioning base stations and the characteristics of the received impulse signal.

Thus, based on the high-accuracy positioning technique such as UWB, coordinate information of the athlete's position can be collected in real time, and then, the coordinate information can be aggregated into one position server through the UWB communication technique, and the position server can perform a real-time processing (e.g., connection depiction, error information removing, or the like) on the coordinate information to calculate the athlete's displacement per unit time and calculate motion information such as data of a real-time speed. In turn, the position server can calculate and draw out a moving track of the athlete's entire movement accurately by calculating and analyzing all of sampling points in the entire procedure of the athlete's games or training in real time in combination with information of time coordinates on the sampling points.

In the embodiments of this disclosure, in order to transmit wireless signals to the outside or receive wireless signals from outside, at least a part of the second wireless communication unit 124 is arranged not to be blocked by insulators in the apparatus 100 as much as possible, so as to increase intensity of transmission and reception of the wireless signals.

In particular, in order to implement wireless communication transmission, in one embodiment, the second wireless communication unit 124 includes: a radio frequency module for converting data to be transmitted including the user data or the beacon data for positioning into a radio-frequency signal in real time; and an antenna module for radiating the radio-frequency signal outwards. For example, the antenna module is provided on the outer surface 110b.

In one embodiment, in order to maximize a radiation intensity of the signal, preferably, the antenna module is printed or embedded directly on the outer surface 110b in a form of a flexible circuit.

Hereinafter, a detailed configuration of the antenna module will be described in detail in one specific example with reference to FIG. 5. In the specific example, it assumes that the smart sports protective apparatus is a leg guard. It is obvious that, without redundant description, the configuration of the antenna module can also be applied in other sports protective apparatus such as a wrist guard, a knee guard, or the like.

Figure 5:
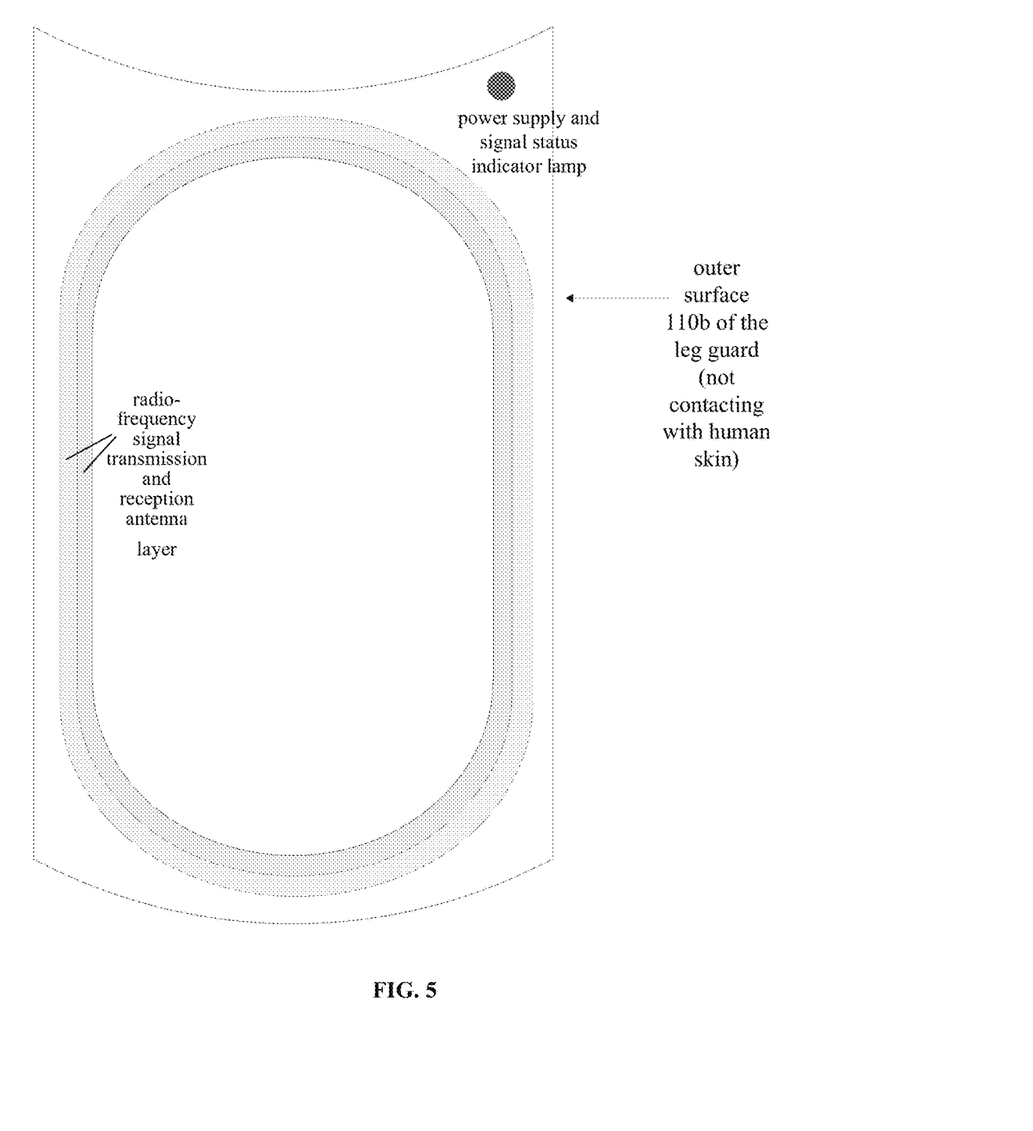
FIG. 5 illustrates a schematic diagram of an antenna module according to a specific example of the embodiments of this disclosure.

FIG. 5 illustrates a schematic diagram of an antenna module according to a specific example of the embodiments of this disclosure.

As shown in FIG. 5, a dual-ring shaped antenna module is arranged on the outer surface 110b of the smart leg guard. This antenna module is integrated with the leg guard in the form of the flexible circuit, and is printed or embedded on the outside surface of the leg guard directly. Such annular ring-like arrangement can enable the antenna module to use the largest area of coils to transmit and receive radio-frequency signals, so as to achieve a good effect in positioning and signaling.

Further, in order to know whether the leg guard is in working status, a signal lamp can be arranged on the outer surface 110 of the leg guard (for example, an indicator lamp of power supply and signal status is provided at the upper right corner of the leg guard, as shown in FIG. 5). As shown, the outer surface of the leg guard can still be a smooth curved surface without any projecting structure, thus only a minor modification is made to the appearance design of the leg guard currently popular on the market, which significantly satisfies people's traditional aesthetical standard.

In order to save cost and maximize usage of elements, in one embodiment, the second wireless communication unit can share one antenna module with the first wireless communication unit and the motion sensing module 1213 mentioned above.

With reference back to FIG. 2, in the embodiments of this disclosure, since the data collecting unit 121 can be various types of sensors and its collected user data may be analog signals or digital signals, in one embodiment, in order to store and transmit such signals, these user data can be converted into a unified format of data signal by the data processing unit 125 for subsequent processing. That is, the data processing unit 125 can perform format conversion, encoding and encryption, or the like on the user data collected by the data collecting unit 121.

Further, in order to realize an optimal processing efficiency, in the embodiments of this disclosure, the second processing unit 126 can control the wireless transmission operation of the second wireless communication unit 124. And, the second processing unit 126 can also control the format conversion operation of the data processing unit 125. For example, the second processing unit 126 can encapsulate, encrypt, or pre-process the required data, and manage communication of all data of the apparatus 100 between the base stations and the system. Obviously, this disclosure is not limited to this. The first processing unit 122 and the second processing unit 126 can also be integrated into one processing unit.

Preferably, in case of adopting two independent processing units, in order to improve utilization efficiency of the electric power of the circuit device 120, in one embodiment, the power managing unit 127 is further adopted to control power supply of the two processing units separately. That is, the power managing unit 127 can selectively supply the electric power from the power supply device 130 to the first processing unit 122 and/or the second processing unit 126 according to the user's usage requirement.

For example, in a case that a real-time data collection with high precision is required, the second processing unit 126 is turned on through the power managing unit 127, so that the second processing unit 126 executes interaction of UWB signals with the receiving base stations (positioning base stations) to implement the positioning operation with high precision. In contrast, in a case that the real time data collection with high precision is not required or in a field where the receiving base stations are not provided or currently not available, the second processing unit 126 is turned off, so that the smart sports protective apparatus can no longer connect and communicate with the receiving base stations, so as to reduce unnecessary power consumption to extend its stand-by time.

In the latter case, in order to ensure a continuous evaluation on the athlete's position information, the apparatus 100 can still use modules such as a Bluetooth® communication module, a GPS module or the like to connect with other mobile terminals (for example, smart phones) to carry out the analysis and evaluation in the mobile terminal locally. Then, the mobile terminal can execute data exchange with a cloud-end server through Internet or the like, so as to transmit related evaluation data to the cloud-end server for storage and further processing.

In other words, after disconnecting from the high-accuracy positioning system based on the base stations, the apparatus 100 (for example, the smart leg guard) can still perform the positioning operation by using a built-in GPS module and connect with the smart phone by using, for example, the Bluetooth® module to execute the data communication. Thus, when the user takes training or plays sports in a field without the positioning base stations, various kinds of user data can be sent to the cloud-end server through for example a specific application (App) installed in the smart phone, for subsequent processing. At this time, the power managing unit 127 controls the positioning system with high precision (the second processing unit 126) to enter into a sleeping status. For example, the power managing unit 127 can be triggered to switch between different modes (for example, entering into the sleeping status or entering into a wake-up status) by a power switch button provided on the apparatus 100, or an adaptive adjustment of the power managing unit 127 can also be triggered according to whether GPS positioning information or UWB system information is generated in the smart protective apparatus.

At last, with reference back to FIG. 1, in the apparatus 100, the power supply device 130 can provide the electric power to the circuit device 120, to implement above-described various kinds of system functions.

In order to reduce sizes of electric devices so as to reduce an overall dimension of the apparatus 100, in one embodiment, the circuit device 120 and the power supply device 130 can be formed integrally, and be tiled in the same direction in the base body device 110 (as shown in FIG. 4).

Further, in order to charge and maintain the apparatus 100, in one embodiment, the circuit device 120 and the power supply device 130 can be provided in the base body device 110 in a detachable manner.

Thus, by integrating a battery with a main board, the battery of the smart sports protective apparatus can be replaced, and meanwhile the same main board can be used in different smart sports protective apparatus, so that consistency of the user data is ensured sufficiently.

Hereinafter, configurations of the circuit device 120 and the power supply device 130 are described in detail in one specific example with reference to FIG. 6. In the specific example, it assumes that the smart sports protective apparatus is a leg guard. It is obvious that, without redundant description, the configurations of the circuit device 120 and the power supply device 130 can also be applied in other sports protective apparatus such as a wrist guard, a knee guard, or the like.

Figure 6:
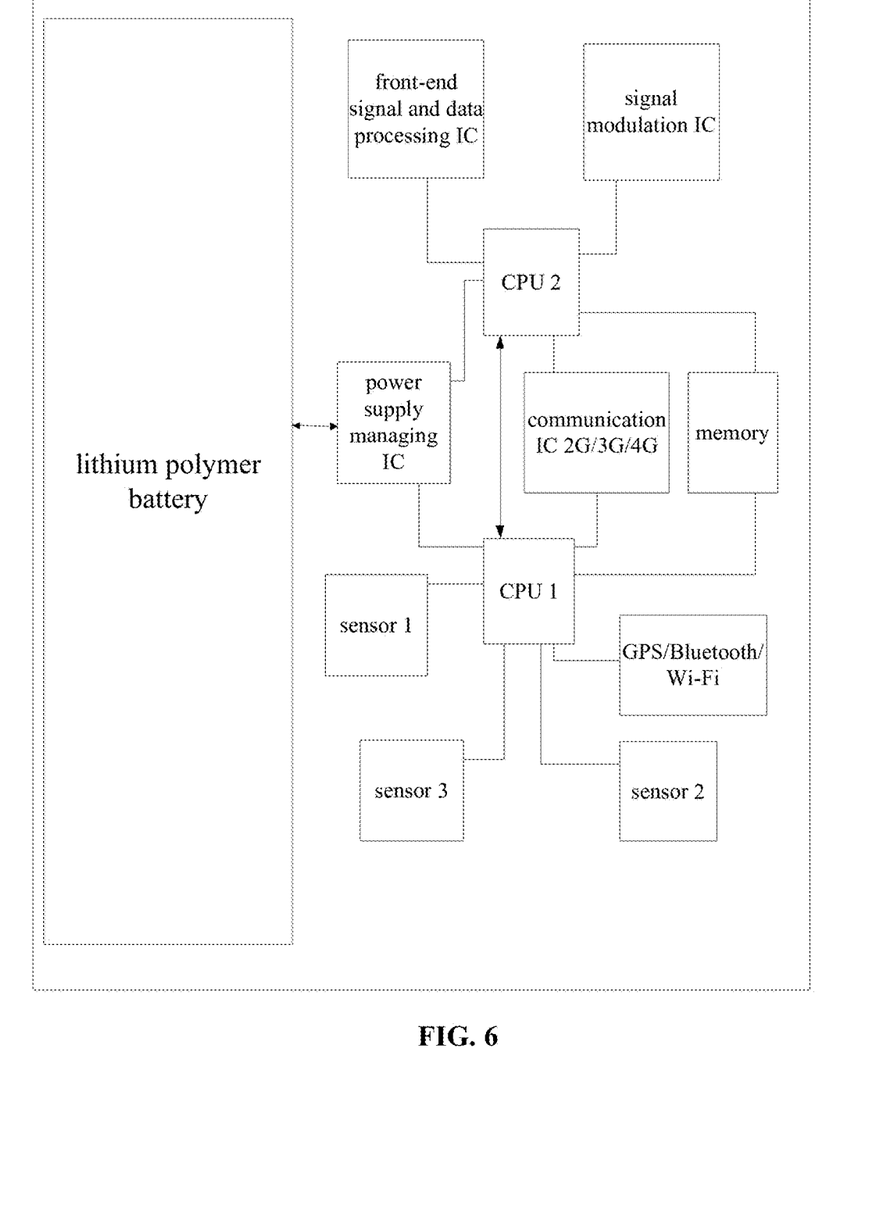
FIG. 6 illustrates a schematic diagram of a circuit device and a power supply device according to a specific example of the embodiments of this disclosure.

FIG. 6 illustrates a schematic diagram of a circuit device and a power supply device according to a specific example of the embodiments of this disclosure.

As shown in FIG. 6, the circuit device 120 adopts a design of dual central processing units (CPUs), in which one CPU (CPU1 in FIG. 6) corresponds to the first processing unit 122 which is responsible for managing a bottom-layer data collection and pre-processing and communication with other parts, and the other CPU (CPU2 in FIG. 6) corresponds to the second processing unit 126 which is responsible for managing data transmission and positioning. As described above, when only a part of the functions is needed, only a part of the system is allowed to power on by using a power supply managing IC to adopt different setting modes for the power supply, so as to reduce power consumption of running of the entire system. The power supply managing IC corresponds to the power managing unit 127.

Sensor 1 to sensor 3 in FIG. 6 correspond to the data collecting unit 121 for collecting the user data including the user's biological data and body gesture data.

Memory in FIG. 6 corresponds to the storing unit 123 for storing the user data collected by the various sensors.

A GPS module in FIG. 6 corresponds to the data collecting unit 121 for collecting the user data including the user's motion status data.

A Bluetooth®/Wi-Fi module in FIG. 6 corresponds to the first wireless communication unit 128 for transmitting the user data to the mobile terminal wirelessly.

A front-end signal and data processing chip (IC) in FIG. 6 corresponds to the data processing unit 125 for performing pre-processing on the collected original signals (including analog signals and digital signals) and performing corresponding program function control, so as to convert the original signals into data format as required.

A signal modulation IC and a communication IC in FIG. 6 correspond to the second wireless communication unit 124. In particular, the signal modulation IC is responsible for modulating ultra high frequency (UHF) signals before its transmission in the radio frequency, and the communication IC is responsible for data exchange with the base stations or up-stream equipment and corresponding control.

Hereinafter, steps of using the smart sports protective apparatus according to the embodiments of this disclosure is described in brief.

Firstly, the athlete (or the user) wears the smart sports protective apparatus in sports games or training. There is no difference in wearing procedure between the smart sports protective apparatus and the conventional ones, and thus the athlete will feel the same and will not have any uncomfortable feeling. Then, the apparatus can communicate with a real-time high-frequency collecting apparatus arranged around a sports field or a training field, or connect with information capturing points (e.g., access points or hot spots) outside the fields directly by using other network connecting manners such as UWB, Bluetooth®, wireless fidelity (Wi-Fi), or the like. Next, the apparatus can transfer captured information to a back-end process in real time through wired or wireless networks, and the back-end process corrects the acquired data and stores it in the cloud-end server. Finally, the server can simulate the athlete's physical condition and motion gesture according to a precise algorithm, and present them in front-end by using portable electronic apparatus such as a portable mobile phone or the like.

Further, various kinds of data stored and analyzed in the server can be stored in encryption for historical review. For this reason, preferably, a unique identifier can be assigned to each smart sports protective apparatus, so that one apparatus can be only used by one and the same user. That is, one apparatus can be used by only one user for the entire time, and not be shared among a plurality of users. Once the apparatus is damaged, it will be repaired according to real-name registration information, so as not to influence collection and storage of the original user's historical data.

In summary, the embodiments of this disclosure rebuild functions and structures of the conventional sports protective apparatus intelligently, and make it further have certain smart functions in addition to the conventional protection function. In particular, in the smart sports protective apparatus according to the embodiments of this disclosure, the antenna module for a UWB positioning system can be equipped on an outer surface layer of the apparatus for positioning and data transmission; and bio sensors for measuring the heart rate, the blood oxygen, the myoeletricity, or the like can be arranged at the inner surface of the apparatus contacting with the skin; and a main circuit board and a battery can be arranged at the solidest position of the apparatus (sandwiched between the outer and inner surfaces) to avoid being damaged. Further, parts of the main board and the battery can be made into detachable parts to be attached to or detached from different smart sports protective apparatus according to user requirements, and a charging interface for charging the battery is arranged at an end or a side of the apparatus, so that the apparatus can be placed on a dedicated charging device (for wireless charging) or be charged via a dedicated charging cable.

By the above-described configuration, the smart sports protective apparatus according to the embodiments of this disclosure realizes the following functions including: (1) real-time and accurate measurement of the athlete's motion velocity (a measuring error thereof can be less than 0.1-0.3 meters per second); (2) reproduction of the athlete's moving track; (3) real-time collection of the athlete's related physiological index to reflect the athlete's physical condition; (4) real-time display of the athlete's body gesture; (5) evaluation of performance efficiency of related skilled actions and evaluation of comprehensive athletic ability; and (6) real-time transmission of all related data to the server according to the requirements for being analyzed comprehensively and stored.

And, in the embodiments of this disclosure, after collecting real-time data of related motion and various kinds of physiological information (including but not limited to the velocity, the body gesture, the heart rate, the pulse, the blood oxygen, the blood pressure, the electrocardio, the body temperature, or the like) of the athlete in the entire procedure of the games or training, the athlete's body status at any time point can be reproduced by analyzing the collected data in real time through various kinds of hardware apparatus, algorithms and software platforms, so as to provide a scientific reference for the athlete's training and evaluation.

As compared with the conventional smart hand ring, more types of sensors are built in the smart sports protective apparatus according to the embodiments of this disclosure to collect more user data in a more accurate way, so as to calculate the athlete's physical condition and body gesture comprehensively. And, the apparatus can measure the athlete's movement velocity in real time by using the precise positioning techniques such as UWB, thus the timeliness and the accuracy thereof is much better than the smart hand ring. And, since no additional apparatus is equipped on the athlete's body, there is no uncomfortable feeling generated when he is playing sports, which ensures that he can play in his/her normal performance level.

Taking football as an example, in football games, leg guards are essential equipment for each player. The smart leg guard according to the embodiments of this disclosure can conveniently collect real-time data related to the football game for later analysis while protecting the player's body from injuries without adding additional equipment, so as to help the player take training and improve achievement more scientifically. Further, by improvement in material and structure, there is no difference in wearing between the smart leg guard and the conventional leg guard.

Thus it can be seen that the embodiments of this disclosure can solve problems of real-time collection, storage, and transmission of data in the athlete's sports activities (e.g., football), which is beneficial for the athlete's coach, trainer, parents, or the like to analyze the athlete's physical condition, motion status, or the like. And, the athlete's moving track can be played back as required, which enables the coach or other people to know the athlete's comprehensive data. Further, in the application of sports tutoring, it enables parents to observe their children's body status and summarize their progress through presentation of instant data and long term data. Further, since it can transmit the collected athlete's position coordinates as the real-time game data to simulate the actual game scene in real time, the real-time game data of any geographic regions, any skill level, and any age groups can be reproduced and visualized all over the whole country or even the whole world. Moreover, it facilitates a massive data collecting work for game players, and can refine the sports training and identify talented players by analysis on the massive data, so as to improve the training efficiency of the football or other athletics sports greatly.

While some embodiments of this disclosure have been described, these embodiments have been presented by way of example only, and are not intended to limit the scope of this disclosure. Indeed, the novel apparatus, methods and systems described herein may be embodied in a variety of other forms; furthermore, various omissions, substitutions and changes in the form of the apparatus, methods and systems described herein may be made without departing from the spirit of this disclosure. The accompanying claims and their equivalents are intended to cover such forms or modifications as would fall within the scope and spirit of this disclosure.

The invention claimed is:

1. A smart sports protective apparatus, comprising:

a base body device for covering at least a part of a user's body to relieve an impact of an external force to at least the part of the user's body when the user is playing sports;

a circuit device for collecting user data, including the user's biological data, motion status data, and body gesture data, from the user in real time when the user is playing sports, at least a part of the circuit device being arranged inside the base body device; and a power supply device for supplying an electric power to the circuit device, the power supply device being arranged inside the base body device, the circuit device and the power supply device being formed integrally and being tiled in the base body device, the circuit device comprising:

a data collecting unit for collecting the user data, and the data collecting unit including    a biosensing module for collecting the user's biological data,    a gesture sensing module for collecting the user's body gesture data, and    a motion sensing module for collecting the user's motion status data; and a first processing unit for controlling the collecting operations of the data collecting unit, at least a part of the biosensing module being arranged on an inner surface of the base body device contacting with the user's body, and the biosensing module comprising at least one of:

a heart rate sensor for detecting data of a real-time heart rate of the user, an electrocardio sensor for detecting data of a real-time electrocardo of the user, a pulse sensor for detecting data of a real-time pulse of the user, a blood oxygen sensor for detecting data of a real-time blood oxygen of the user, a body temperature sensor for detecting data of a real-time body temperature of the user, a myoeletricity sensor for detecting data of a real-time myoeletricity of the user, and a blood pressure sensor for detecting data of a real-time blood pressure of the user, at least one of the heart rate sensor, the electrocardio sensor, the pulse sensor, and the blood oxygen sensor comprising an optical transceiver which, when the base body device covers at least the part of the user's body, emits and receives light in a closed space formed by the base body device and at least the part of the user's body without being influenced by external light, the circuit device further comprising:

a first wireless communication unit for transmitting the user data to a mobile terminal wirelessly;

a second wireless communication unit for transmitting the user data to a server wirelessly via a base station apparatus, at least a part of the second wireless communication unit being arranged not to be blocked by insulators in the smart sports protective apparatus; and a second processing unit for controlling the wireless transmission operation of the second wireless communication unit.

2. The smart sports protective apparatus of claim 1, wherein the smart sports protective apparatus is a smart leg guard, in which the base body device covers at least a part of the user's shank to relieve the impact of the external force to the user's shank when the user is playing sports, to prevent the user's shank from being injured.

3. The smart sports protective apparatus of claim 1, wherein the myoeletricity sensor comprises two electrodes provided at the same height and at two outermost edges of the inner surface respectively.

4. The smart sports protective apparatus of claim 1, wherein the gesture sensing module is provided between an inner surface of the base body device contacting with the user's body and an outer surface of the base body device not contacting with the user's body, and    the gesture sensing module comprises at least one of a gyroscope sensor for detecting data of a real-time inclination and rotation angle of the user, an acceleration sensor for detecting data of a real-time acceleration of the user, a geomagnetic field sensor for detecting data of a real-time orientation or direction of the user, and an air pressure sensor for detecting data of a real-time altitude and air pressure of the user.

5. The smart sports protective apparatus of claim 1, wherein at least a part of the motion sensing module is provided between an inner surface of the base body device contacting with the user's body and an outer surface of the base body device not contacting with the user's body, and    the motion sensing module comprises a satellite signal receiver for receiving satellite signals from a plurality of satellite signal transmitters, so as to determine data of a real-time position of the user according to signal parameters of the satellite signals respectively received from the plurality of satellite signal transmitters and known data of positions of the plurality of satellite signal transmitters.

6. The smart sports protective apparatus of claim 5, wherein the satellite signal receiver and the plurality of satellite signal transmitters comply with a global positioning system (GPS) standard.

7. The smart sports protective apparatus of claim 1, wherein the circuit device further comprises a storing unit for storing the user data.

8. The smart sports protective apparatus of claim 1, wherein the first wireless communication unit complies with at least one of communication standards including Bluetooth® and wireless Fidelity.

9. The smart sports protective apparatus of claim 1, wherein based on the user data, the server performs at least one of displaying the user data, at a specific time, calculating the user's displacement during a specific time period, calculating the user's velocity at a specific time, calculating the user's average velocity during a specific time period, calculating the user's maximum velocity and minimum velocity during a specific time period, calculating the user's acceleration at a specific time, drawing the user's moving track during a specific time period, analyzing the user's physiological status at a specific time, presenting the user's body gesture at a specific time, analyzing a performance quality and a timeliness of the user's specific skilled action, and evaluating the user's athletic ability, skill level, and/or training result.

10. The smart sports protective apparatus of claim 1, wherein the second wireless communication unit further transmits beacon data to a plurality of base station apparatus, so as to determine data of a real-time position of the user according to signal parameters of the beacon data respectively received by the plurality of base station apparatus and known data of positions of the plurality of base station apparatus.

11. The smart sports protective apparatus of claim 1, wherein the second wireless communication unit and the base station apparatus comply with at least one of communication standards including ultra wide band (UWB), chirp spread spectrum (CSS), and mobile communication.

12. The smart sports protective apparatus of claim 10, wherein the second wireless communication unit comprises:
- a radio frequency module for converting data to be transmitted into a radio-frequency signal in real time, the data to be transmitted including the user data or the beacon data; and
- an antenna module for radiating the radio-frequency signal outwards, the antenna module being provided on an outer surface of the base body device not contacting with the user's body.

13. The smart sports protective apparatus of claim 12, wherein the antenna module is printed or embedded on the outer surface directly in a form of a flexible circuit.

14. The smart sports protective apparatus of claim 1, wherein the circuit device further comprises a power managing unit for selectively supplying the electric power from the power supply device to the first processing unit and/or the second processing unit according to the user's usage requirement.

15. The smart sports protective apparatus of claim 1, wherein the circuit device and the power supply device are provided in the base body device in a detachable manner.

* * * * *